US00PP17288P2

(12) United States Plant Patent
Danziger

(10) Patent No.: US PP17,288 P2
(45) Date of Patent: Dec. 19, 2006

(54) ***PETUNIA* PLANT NAMED 'DANCAS 110'**

(50) Latin Name: *Petunia sensu Wijsman*
Varietal Denomination: Dancas110

(75) Inventor: Gabriel Danziger, Moshav Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 0 days.

(21) Appl. No.: 11/236,798

(22) Filed: Sep. 28, 2005

(51) Int. Cl.
*A01H 5/00* (2006.01)

(52) U.S. Cl. ..... Plt./356
(58) Field of Classification Search ..... Plt./356
See application file for complete search history.

*Primary Examiner*—Anne Marie Grunberg
*Assistant Examiner*—Georgia Helmer
(74) *Attorney, Agent, or Firm*—Foley & Lardner LLP

(57) ABSTRACT

A new and distinct *Petunia* plant named 'Dancas110' characterized by having medium, yellow flowers; floriferous blooming; blooms in early season; mounded growth habit; and suitable for patios and outdoors bedding.

2 Drawing Sheets

Botanical designation: *Petunia sensu Wijsman.*
Variety denomination: 'Dancas110'.

BACKGROUND OF THE INVENTION

The present invention relates to a new and distinct cultivar of *Petunia* plant, botanically known as *Petunia sensu Wijsman*, hereinafter referred to by the cultivar name 'Dancas110'.

The new cultivar originated from cross-made in a controlled breeding program in Moshav Mishmar Hashiva, Israel. The female parent is a *Petunia sensu Wijsman* propriety cultivar designated 'CV-6309' (unpatented). The male parent is a *Petunia sensu Wijsman* propriety cultivar designated 'CV-6124' (unpatented). 'Dancas110' was discovered and selected by the Inventor, Gabriel Danzinger, as a single flowering plant within the progeny of the stated cross in a controlled environment in Moshav Mishmar Hashiva, Israel.

Asexual reproduction of the new cultivar by cutting of side shoots, was first performed in June of 2002 in Moshav Mishmar Hashiva, Isreal, and has demonstrated that the combination of characteristics as herein disclosed for the new cultivar are firmly fixed and retained through successive generations of asexual reproduction. The new cultivar reproduces true-to-type.

BRIEF SUMMARY OF THE INVENTION

The following traits have been repeatedly observed and are determined to be unique characteristics of 'Dancas110' which in combination distinguish this *Petunia* as a new and distinct cultivar:

1. Medium in size, yellow colored flowers;
2. Very floriferous;
3. Mounded growth habit;
4. Early to bloom; and
5. Suitable for patios and outdoors bedding.

Plants of 'Dancas110' differ from plants of the parental cultivars, 'CV 6309' (unpatented) and 'CV-6124' (unpatented), in the following characteristics described in Table 1:

TABLE 1

| Character | New Cultivar 'Dancas110' | Female Parent 'CV-6309' (unpatented) | Male Parent 'CV-6124' (unpatented) |
|---|---|---|---|
| Flowering time | Early, Spring | Early, Spring | Late, Summer |
| Flower size | Medium<br>Diameter: 5 cm<br>Depth: 3.5 cm | Small<br>Diameter: 4 cm<br>Depth: 3 cm | Medium<br>Diameter: 5 cm<br>Depth: 3.5 cm |
| Growth habit | Mounded, Bushy | Compact, Bushy | Moderately vigorous and not well branched |

Of the many commercial cultivars known to the present Inventor, the most similar in comparison to 'Dancas110' is the *Petunia sensu Wijsman* cultivar 'Danpetblu' (unpatented and disclosed in pending U.S. patent Application Ser. No. 11/128,292. Plants of 'Dancas110' differ from plants of 'Danpetblu' in the following characteristics described in Table 2:

TABLE 2

| Character | New Cultivar 'Dancas110' | Comparison Cultivar 'Danpetblu' (unpatented) |
|---|---|---|
| Flowering time | Early, Spring | Medium, Summer |
| Flower color | Yellow | Blue |
| Growth habit | Bushy Mound | Compact and cascading |

BRIEF DESCRIPTION OF THE DRAWINGS

The accompanying colored photographs illustrate the overall appearance of the new *Petunia* cultivar 'Dancas110' showing the colors as true as is reasonably possible with colored reproductions of this type. Colors in the photographs may differ slightly from the color values cited in the detailed botanical description which accurately describe the color of the 'Dancas110'.

DETAILED BOTANICAL DESCRIPTION

Figure 1:
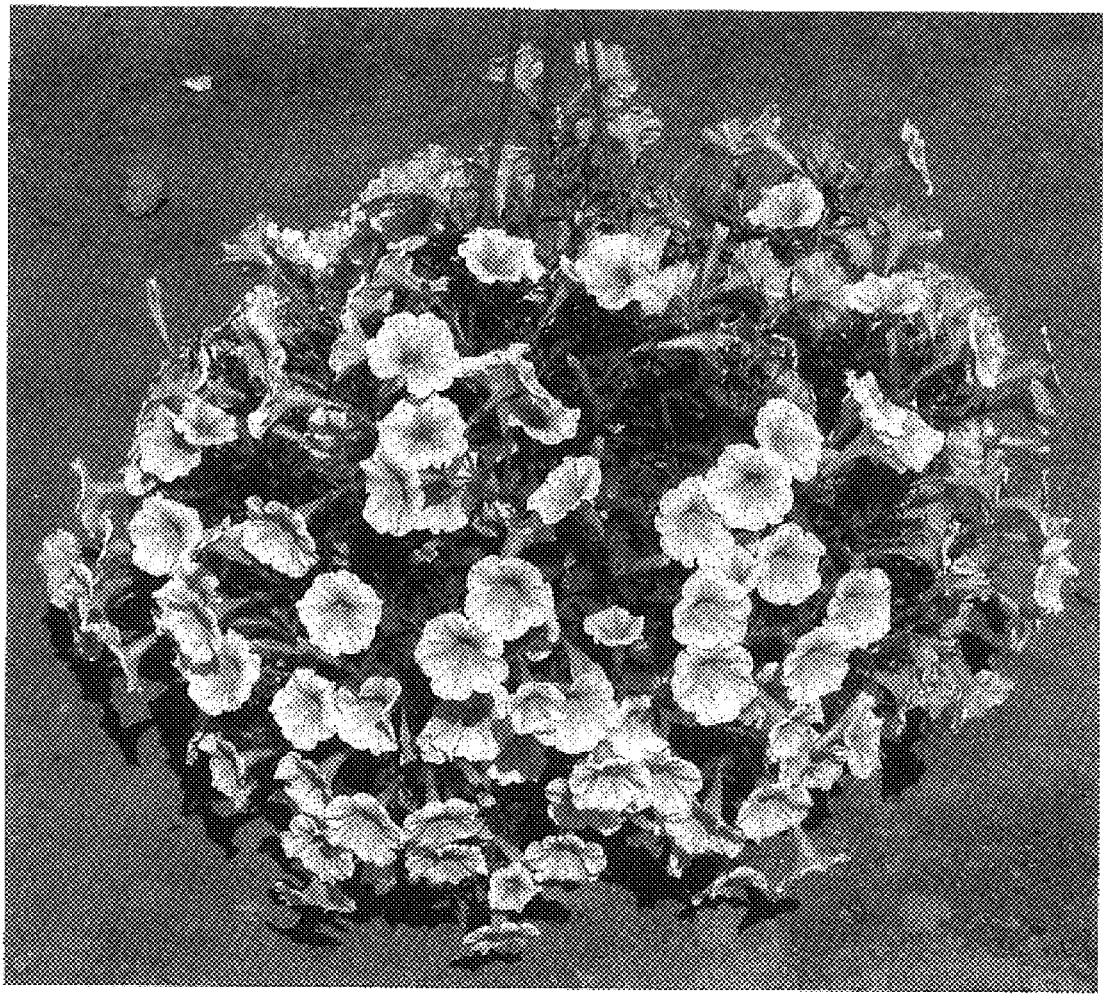
FIG. 1 shows a side perspective view of a typical flowering plant of 'Dancas110' in a plant hanger, at 3 months of age.
Figure 2:
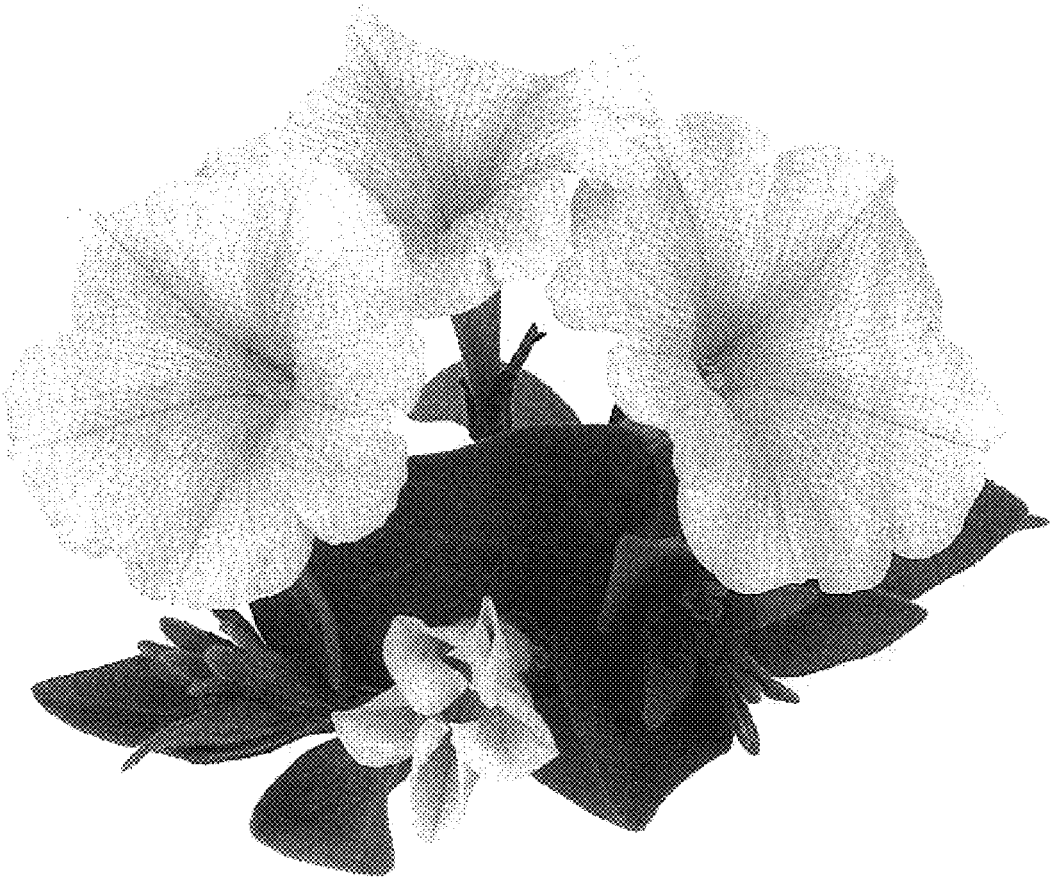
FIG. 2 shows a close-up view of the typical flowers and leaves of 'Dancas110' at 3 months of age.

'Dancas110' has not been observed under all possible environmental conditions. The phenotype of the new cultivar may vary with variations in environment such as temperature, light intensity, and day length without any change in the genotype of the plant. The following observations, measurements and values describe the new cultivar as grown in Moshav Mishmar Hashiva, Israel, under conditions which closely approximate those generally used in commercial practice.

Plants of 'Dancas110' are grown outdoors in a moderate climate, and grown indoors during the winter. Irrigation and fertilization are needed on a regular basis. For optimal growth, grow plants of 'Dancas110' in full sunlight. Plants of 'Dancas110' are fully grown in 3 months when grown in full sunlight, and bloom all year-round in a moderate climate. 'Dancas110' is used as a potted plant and bedding plant.

Color references are made to The Royal Horticultural Society Colour Chart (R.H.S.), 2001 edition, except where general colors of ordinary significance are used. Color values were taken under daylight conditions at approximately 12:00 noon in Moshav Mishmar Hashiva, Israel. The age of the plant described is 3 months.

Parentage:
- *Male parent.*—*Petunia sensu Wijsman* propriety cultivar designated 'CV-6124' (unpatented).
- *Female parent.*—*Petunia sensu Wijsman* propriety cultivar designated 'CV-6309' (unpatented).

Classification:
- *Botanical.*—*Petunia sensu Wijsman.*
- *Commercial.*—*Petunia* cv. *Petunia* Sunray.

Propagation: Cutting of side shoots.

Plant:
- *General appearance and form.*—Height: 25 cm. Spread: 50 cm.
- *Growth habit.*—Mounded.
- *Growth rate.*—Fully grown plant in 3 months.
- *Branching habit and description.*—Freely branching, more than typical *Petunia* species.
- *Flowering response.*—Long day facultative.
- *Flowering season.*—Year round in moderate climate.
- *Winter hardiness/weather tolerance.*—Frost tender. Plants may be damaged by temperatures below 5° C.
- *Lastingness of the individual bloom.*—2 to 4 days.
- *Rooting habit.*—From cutting base.
- *Time to initiate roots.*—1 week.
- *Time to produce a rooted cutting.*—2 to 3 weeks.
- *Fragrance.*—None.

Stem description:
- *Length.*—5 to 60 cm.
- *Diameter.*—0.5 to 0.6 cm.
- *Strength.*—Medium.
- *Branching.*—Freely.
- *Pubescence.*—Yes.
- *Internode length.*—2.5 to 3.0 cm.
- *Internode and stem color.*—Yellow-Green Group, RHS 144A.

Foliage:
- *Arrangement.*—Alternate.
- *Overall shape of leaf.*—Elliptic.
- *Apex.*—Obtuse.
- *Base.*—Acute.
- *Length.*—4 to 6 cm.
- *Width.*—2 to 4 cm.
- *Margin.*—Entire.
- *Texture.*—Lustrous.
- *Color of upper surface.*—Mature leaf: Yellow-Green Group, RHS 147 A. Immature leaf: Yellow-Green Group, RHS 146 A.
- *Color of lower surface.*—Mature leaf: Yellow-Green Group, RHS 146 A. Immature leaf: Yellow-Green Group, RHS 146A.
- *Venation pattern.*—Pinnate.
- *Venation color.*—Yellow-Green Group, RHS 144C. Upper surface: Yellow-Green Group, RHS 144C. Lower surface: Yellow-Green Group, RHS 144C.
- *Petiole.*—Length: 1.0 to 2.0 cm. Diameter: 0.2 cm. Color: Yellow-Green Group, RHS 144C.

Inflorescence:
- *Flower longevity.*—2 to 4 days.
- *Flower size.*—Diameter: 4 cm. Depth: 3 cm.
- *Floral tube.*—Diameter: 0.7 to 1.0 cm at the corolla surface.
- *Flower shape/type.*—Trumpet.
- *Average number of flowers per lateral branch.*—6 to 8.
- *Petals.*—Number: 5; (all the 5 petals are united). Length: 4 to 5.5 cm (from edge of the petal up to the base of floral tube). Width: 4.5 cm across. Shape: Corolla united with 5 lobes and a long straight tube. Apex: Truncate. Margin: Entire. Texture: Glabrous. Color: Upper surface: Center: Yellow Group, RHS 2 A; Margin: White Group, RHS 2 D. Lower surface: Base: Green-Yellow Group, RHS 1 B; Margin: White Group, RHS 1 D.
- *Sepals.*—Number: 5. Length: 1.2 to 1.5 cm. Width: 0.1 to 0.2 cm. Shape: Lanceolate. Apex: Truncate. Margin: Entire. Texture: Lustrous. Color: Upper surface: Green Group, RHS 137 A. Lower surface: Green Group, RHS 137 B.
- *Bud.*—Rate of opening: 7 to 10 days. Color: Yellow-Green Group, RHS N144 C. Shape: Tubular. Length: 3 to 4 cm. Diameter: 0.3 to 0.9 cm.
- *Peduncle.*—Color: Green Group, RHS 137 B. Length: 2 to 3 cm.

Reproductive organs:

Androecium:
- *Stamen.*—Number: 5. Color: Green Group, RHS 130 D.
- *Anthers.*—Color: Yellow Group, RHS 2 D.
- *Filament.*—Color: Green Group, RHS 130 D.
- *Pollen.*—Color: Yellow Group, RHS 2 D.

Gynoecium:
- *Pistil.*—Length: 2.5 cm. Color: Yellow-Green Group, RHS 146 C.
- *Stigma.*—Color: Yellow-Green Group, RHS 146 C.
- *Ovary.*—Color: Yellow-Green Group, RHS 146 C.

Seed:
- *Number.*—About 40 to 50.
- *Length.*—1 mm.
- *Width.*—1 mm.
- *Shape.*—Ovoid.
- *Color.*—Brown Group, RHS 200 C.

Fruit:
- *Number.*—Few, when naturally pollinated.
- *Length.*—8 mm.
- *Width.*—4 mm.
- *Shape.*—Ellipsoid.
- *Color.*—Grey-Brown Group, RHS 199 A.

Disease resistance: No information currently available.

I claim:

1. A new and distinct *Petunia* plant named 'Dancas110', substantially as illustrated and described herein.

* * * * *